(12) United States Patent
Yang et al.

(10) Patent No.: US 6,329,512 B1
(45) Date of Patent: Dec. 11, 2001

(54) IMMUNOGENIC CONJUGATE MOLECULES

(75) Inventors: Yan-Ping Yang; Ali Kandil, both of Willowdale; Lucy Gisonni, Toronto; Raafat Emil Fahmy Fahim, Mississauga; Michel Henri Klein, Willowdale, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 08/467,883

(22) Filed: Jun. 6, 1995

Related U.S. Application Data

(63) Continuation of application No. 08/371,965, filed on Jan. 12, 1995, now Pat. No. 5,681,570.

(51) Int. Cl.$^7$ ..................................................... A23J 1/00
(52) U.S. Cl. ..................... 530/412; 530/418; 530/422; 424/197.11; 424/203.1; 424/256.1
(58) Field of Search ................... 424/197.11, 203.1, 424/234.1, 244.1, 256.1; 530/412, 418, 422

(56) References Cited

U.S. PATENT DOCUMENTS 5,141,743    8/1992   Schryvers .

FOREIGN PATENT DOCUMENTS

| | | |
|---|---|---|
| WO 92/10936 | 1/1992 | (WO) . |
| WO 94/14195 | 8/1993 | (WO) . |
| WO 94/12641 | 11/1993 | (WO) . |

OTHER PUBLICATIONS

Loeb, M.R. 1987. "Protection of Infant Rats from *Haemophilus influenzae* Type b Infection by Antiserum to Purified Outer Membrane Protein a." Infection and Immunity 55(11):2612–2618.

Austrian, R. 1987. Pneumococcal infections. In Harrison's Principles of Internal Medicine. 11th ed. E. Braunwald, K.J. Isselbacher, R.G. Petersdorf, J.D. Wilson, J.B. Martin, and A.S. Fauci (ed), McGraw–Hill, New York. 533–537.

Chommaitree, T., and V.M. Howie. 1987. Bacteriology of otitis media. p. 231–247. In J. Berstein and P. Ogra (ed.), Immunology of the ear. Reven Press, New York.

Giebink, G.S. 1989. The microbiology of otitis media. Pediatr. Infect. Dis. J. 8:518520.

Austrian, R. 1981. Some observations on the pneumococcus and on the current status of pneumococcal disease and its prevention. Rev. Infect. Dis. 3 (suppl):S1–S17.

Chu, C.Y., R. Schneerson, J.B. Robbins, and S.C. Rastogi. 1983. Further studies on the immunogenicity of *Haemophilus influenzae* type b and pneumococcal type 6A polysaccharide–protein conjugates. Infect. Immun. 40:245–256.

Schneerson, R., L. Levi, J.B. Robibin, D.M. Bryla, G. Schiffman, and T. Lagergard. 1992. Synthesis of a conjugate vaccine coposed of pneumococcus type 14 capsular polysaccharide bound to pertussis toxin. Infect. Immun. 60:3528–3532.

Fattom, A., C. Lue, S.C. Szu, J. Mestecky, G. Schiffman, D. Bryla, W.F. Vann, D. Watson, J.B. Robbins, and R. Schneerson. 1990. Immune response in adult volunteers elicited by injection of the *Streptococcus pneumoniae* type 12F polysaccharide alone or conjugated to diphtheria toxoid. Infect. Immun. 58:2309–2312.

Robbins, J.B., R. Austrian, C.–J. Lee, S.C. Rastogi, G. Schiffman, J. Henrichsen, P.H. Makela, C.V. Broome, R.R. Facklam, R.H. Tiesjema, and J.C. Parke, Jr. 1983. Considerations for formulating the second–generation pneumococcal capsular polysaccharide vaccine with emphasis on the cross–reactive types within groups. J. Infect. Dis. 148: 1136–1159.

Shapiro, E.D., A.T. Berg, R. Austrian, D. Schroeder, V. Parcells, A. Margolis, R.K. Adair, and J.D. Clemens. 1991. The protective efficacy of polyvalent pneumococcal polysaccharide vaccine. N. Engl. J. Med. 325: 1453–1460.

Deich, R.A., B.J. Metcalf, C.W. Finn, J.E. Farley, and B.A. Green. 1988. Cloning of genes encoding a 15,000–dalton peptidoglycan–associated lipotrotein from *Haemophilus influenzae*. J. Biol. Chem. 170:489–498.

Sarnaik S., J. Kaplan, G. Schiffman, D. Bryla, J.B. Robbins, R. Scheerson. 1990. Studies on pneumococcus vaccine alone or mixed with DT and on pneumococcus type 6B and *Haemophilus influenzae* type b capsular polysaccharide–tetanus toxoid conjugates in 2– to 5–year old children with sikle cell anemia. Pediatr. Infect. Dis. J. 9:181–186.

Weinberg, G.A., D.A. Towler, and R.S. Munson, Jr. 1988. Lipoproteins of *Haemophilus influenzae* type b. J. Bacterol. 170:4161–4164.

(List continued on next page.)

*Primary Examiner*—Jennifer Graser
(74) *Attorney, Agent, or Firm*—Sim & McBurney

(57) ABSTRACT

Immunogenic conjugate molecules comprising at least a portion of a capsular polysaccharide of a Streptococcus strain linked to at least a portion of an outer membrane protein of a Haemophilus strain are provided in which the immunogenicity of the capsular polysaccharide is increased. Particularly capsular polysaccharide from *Streptococcus pneumoniae* are linked to an outer membrane protein of a *Haemophilus influenzae* strain, which protein may be the P1, P2 or particularly the P6 outer membrane protein. Conjugate molecules comprising the P6 protein linked to a capsular polysaccharide from an encapsulated pathogen other than Streptococcus also are described, in which the immunogenicity of the capsular polysaccharide is enhanced. Such conjugate molecules may be incorporated into immunogenic compositions for protecting a host against disease caused by the Streptococcus strain and preferably also the Haemophilus strain. The conjugate molecules and antibodies specific for the capsular polysaccharide or specific for the outer membrane protein may be employed in diagnostic procedures and kits. A process for individually isolating P1, P2 and P6 outer membrane proteins from a Haemophilus strain also is provided.

18 Claims, 5 Drawing Sheets

OTHER PUBLICATIONS

Murphy, T.F., M.B. Nelson, K.C. Dudas, J.M. Mylotte, and M.A. Apicella. 1985. Identification of a specific epitope of *Haemophilus influenzae* on a 16,600–dalton outer membrane protein, J. infec. Dis. 152:1300–1307.

Murphy, T.F., L.C. Bartos, A.M. Campagnari, M.B. Nelson, K.C. Dudas, and M.A. Apicella. 1986. Identification of a 16,600 dalton outer membrane protein of nontypeable *Haemophilus influenzae* as a target for human bactericidal antibody. J. Clin. Invest. 78:1020–1027.

Green, B.A., T. Quinn–Dey, and G.W. Zlotnick. 1987. Biologic activites of antibody to a peptidoglycan–associated lipoprotein of *Haemophilus influenzae* against multiple clinical isolates of *H. influenzae* type b. Infect. Immun. 55:2878–2883.

Munson, R.S. Jr., and D.M. Granoff. 1985. Purification and partial characterization of outer membrane proteins P5 and P6 from *Haemophilus influenzae* type b. Infect. Immun. 49:544–549.

Bradford, M.M. 1976. A rapid sensitive method for the quantitation of microgram quantities of protein utilizing the principle of protein–dye binding. Anal. Biochem. 72:248–254.

Dubois, M., K.A. Gulles, J.K. Hamilton, P.A. Rebers, and F. Smith. 1956. Colorimetric method for the determination of sugars and related substances. Anal. Chem. 28:350–356.

Panezutti, H., O. James, E.J. Hansen, Y. Choi, R.E. Harkness, M.H. Klein and P. Chong. 1993. Identification of surface–exposed B–cell epitopes recognized by *Haemophilus influenzae* type b P1–specific monoclonal antibodies. Infec. Immun. 61: 1867–1872.

Lockhoff, O. Glycolipids as Immunomodulators: Synthesis and Properties. 1991. Chem. Int. Ed. Engl. 30: 1611–11620.

Nixon–George, A., Moran, T., Dionne, G., Penney, C.L., Lafleur, D., Bona, C.A. The adjuvant effect of stearyl tyrosine on a recombinant subunit hepatitis B surface antigen. 1990 J. Immunol. 144: 4798–4802.

Wiesmüller, K.–H., Jung. G., Hess, G. Novel low–molecular weight synthetic vaccine against foot–and–mouth disease containing a potent B–cell and macrophage activator. 1989. Vaccine 8: 29–33.

Deres, et al. 1989, Letters to Nature, In Vivo priming of virus–specific cytotoxic T lymphocytes with synthetic lipopeptide vaccine, vol. 342: 561–564.

Jennings, H.J. Capsular Polysaccharides as Vaccine Candidates. 1990. Current Topics in Microbiology and Immunology 150: 97–127.

Porro et al 1983, Immunoelectrophoretic characterization of the molecular weight polydispersion of polysaccharides in multivalent bacterial capsular polysaccharide vaccines, J. Biol. Stand. 11: 65–74.

Brodeur, B.R., P.S. Tsang, J. Hamel, Y. Larose, S. Montplaisir. 1986. Mouse models for infection for *Neisseria meningitidis B, 2b and Haemophilus influenzae* type b diseases. Can. J. Microbiol. 32:33–37.

IMMUNOGENIC CONJUGATE MOLECULES

"This is a continuation of application Ser. No. 08/371, 965 filed Jan. 12, 1995, now U.S. Pat. No. 5,681,570."

FIELD OF THE INVENTION

The present invention relates to the field of immunology and is particularly concerned with immunogenic conjugate molecules comprising at least a portion of a capsular polysaccharide of a Streptococcus strain linked to at least a portion of an outer membrane protein of a Haemophilus strain.

BACKGROUND OF THE INVENTION

*Streptococcus pneumoniae* is an important human pathogen responsible for pneumonia, meningitis and other invasive diseases throughout the world (ref. 1. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). *S. pneumoniae* is also one of the major three organisms which cause otitis media in infants and children (refs. 2, 3). Otitis media is the most common illness of early childhood with approximately 70% of all children suffering at least one bout of otitis media before the age of seven. Chronic otitis media can lead to hearing, speech and cognitive impairment in children. It is caused by bacterial infection with *S. pneumoniae* (approximately 50%), non-typeable *H. influenzae* (approximately 30%) and *Moraxella (Branhamella) catarrhalis* (approximately 20%). In the United States alone, treatment of otitis media costs between one and two billion dollars per year for antibiotics and surgical procedures, such as tonsillectomies, adenoidectomies and insertion of tympanostomy tubes. Because otitis media occurs at a time in life when language skills are developing at a rapid pace, developmental disabilities specifically related to learning and auditory perception have been documented in youngsters with frequent otitis media.

*S. pneumoniae* is a Gram-positive encapsulated coccus that usually grows in pairs or short chains. The capsules comprise complex polysaccharides and are the basis for dividing pneumococci into different serotypes. *S. pneumoniae* exposed to type-specific antiserum show a positive capsular precipiting reaction, termed the Neufeld quellung reaction, and 84 serotypes have been identified by this means.

A polyvalent pneumococcus vaccine was developed for preventing pneumonia and other invasive diseases due to *S. pneumoniae* in the adult and aging populations. The vaccine contains capsular polysaccharides (CPs) from 23 serotypes of *S. pneumoniae*. These CPs are T-cell-independent antigens. They stimulate mainly immunoglobulin M (IgM) antibody with weak memory and readily induce tolerance. Although anticapsular antibodies to *S. pneumoniae* have long been recognized as protective in adult and immunocompetent individuals, children under 2 years of age and immunocompromised individuals, including the elderly, do not respond well to T-cell independent antigens and, therefore, are not afforded optimal protection by the current pneumococcal vaccines (ref. 4). There is thus a need to improve the current 23-valent pneumococcus vaccine, in order to provide protection for infants and individuals with reduced immuno-responsiveness.

Pneumococcus type 14 is one of the types isolated most frequently from patients of all ages (ref. 8). Pn14 is neutral and is composed of the following repeating tetrasaccharide:

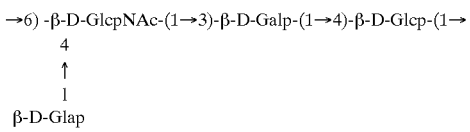

Pn14 is a comparatively poor immunogen among the pneumococcal capsular polysaccharides. In adults, it elicits only a fourfold rise in antibodies in ~80% of vaccinees. This property may be the reason why type 14 pneumococcus is one of the most common types isolated from adult patients immunized with the polyvalent pneumococcal vaccine (ref. 9). Pn14 does not elicit protective levels of antibodies in infants and young children.

CP of Pn6 is another relatively poor antigen in the 23-valent vaccine. Pn6 CP fails to elicit protective levels of antibodies in children up to about 24 months of age and further immunization does not induce a booster response. There are two serotypes of *S. pneumoniae* Pn6, type 6A and type 6B, and the structure of types 6A and 6B pneumococcal polysaccharides differs only in the position of linkage of their α-L-rhamnopyranosyl residues to D-ribitol, which is critical to their relative stabilities. The structures of 6A and 6B polysaccharide are as follows:

Type 6A:→2)α-D-Galp(1→3)-α-D-Glcp(1→3)α-L-Rhap (1→3)-D-ribitol-5-PO$_4$-

Type 6B:→2)α-D-Galp(1→3)-α-D-Glcp(1→3)α-L-Rhap (1→4)-D-Ribitol-5-PO$_4$-

T-cell dependent properties have been conferred to the CP of pneumococcus type 6B (Pn6B) and its immunogenicity improved by covalently coupling it to tetanus toxoid (TT) (ref. 5). CP of pneumococcus type 14 (Pn14) has been conjugated to pertussis toxin (PT) (ref. 6, WO 94/04195). The Pn14-PT conjugate elicited antibodies to Pn14 in mice at levels estimated to be protective in humans and elicited PT neutralizing anti-PT antibodies. Fattom et al. (ref. 7) synthesized conjugates composed of CP from pneumococcus type 12 (Pn12) coupled to diphtheria toxoid (DT). These Pn12-DT conjugates were shown to be more immunogenic than the Pn12 CP alone in adult volunteers.

Diphtheria and tetanus toxoids are frequently used as carriers for poorly immunogenic antigens to produce conjugates. Repeated immunization with these toxoids will produce very high antibody titres to the toxoids which may be disadvantageous. It would be advantageous, therefore, to provide a different carrier for poorly immunogenic carbohydrate antigens, of which there are about six to ten of medical interest. It is also desirable to use a carrier which generates a protective immune response including antibodies that are neutralizing for a further target organism.

P6 is a 16 kDa outer membrane protein (OMP) from *H. influenzae* which constitutes 1 to 5% of the OMP content. The protein is modified by fatty acylation and appears to be analogous to the low-molecular-weight peptidoglycan associated lipoproteins found in other Gram-negative bacteria (refs. 10, 11, 12). P6 has been shown to be present in every non-typeable and typeable *H. influenzae* isolate and is highly conserved (ref. 13). P6 is surface-exposed and is a target for bactericidal human antibodies (ref. 14). Furthermore, antibodies raised against P6 protein provided protection in the infant rat model of bacteremia (refs. 15, 16). These features made P6 a vaccine candidate against meningitis and/or otitis media caused by *H. influenzae*.

SUMMARY OF THE INVENTION

The present invention provides a novel approach to the problem of the poor immunogenicity of capsular polysaccharides of *Streptococcus pneumoniae* or other *Streptococcus strains*, particularly in young children and the immunocompromised.

In accordance with one aspect of the present invention, there is provided an immunogenic conjugate molecule, comprising at least a portion of a capsular polysaccharide of a Streptococcus strain linked to at least a portion of an outer membrane protein of a Haemophilus strain. The at least a portion of the outer membrane protein and at least a portion of the capsular polysaccharide are selected to provide, in the conjugate molecule, an enhanced immune response to the capsular polysaccharide.

The Haemophilus strain providing the outer membrane protein usually is a *Haemophilus influenzae* strain. The outer membrane protein may be any of the various outer membrane proteins of *Haemophilus influenzae*, including the P1, P2, P6, D15 (ref. 20), Hin47 (ref. 21) transferrin receptor, lactoferrin receptor (ref. 22), and hemin binding proteins; particularly the P1, P2 and P6 outer membrane proteins, preferably the P6 protein. The P6 protein may also be linked to at least a portion of a capsular polysaccharide of an encapsulated pathogen, other than Streptococcus in order to provide, in the resulting conjugate molecule, an enhanced immune response to the capsular polysaccharide. Such P6-conjugate molecules form another aspect of the present invention. Such additional capsular polysaccharide may comprise a capsular polysaccharide of *Neisseria meningitidis*, a capsular polysaccharide of *H. influenzae* and a capsular polysaccharide of Group B Streptococcus. The structure of such capuslar polysaccharides as well as identification of other capsular polysaccharides are described in reference 27.

In the one aspect of the invention, the capsular polysaccharide is from a Streptococcus strain and is generally a *Streptococcus pneumoniae* strain. The capsular polysaccharide may be any of the known serotypes, including these having the following structures:

Type 1:

Type 2:

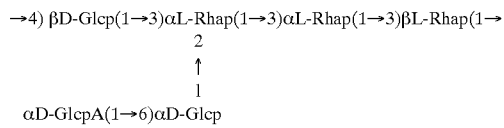

Type 3:

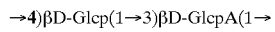

Type 4:

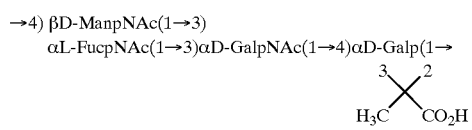

Type 5:

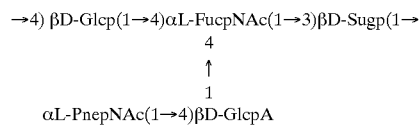

Type 6A:

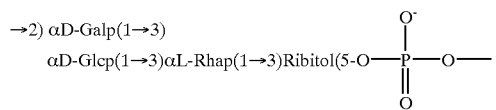

Type 6B:

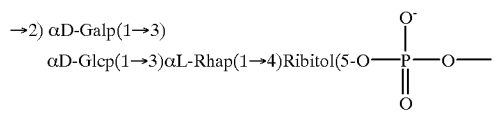

Type 7F:

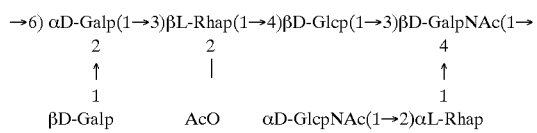

Type 8:

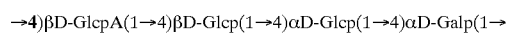

Type 9N:

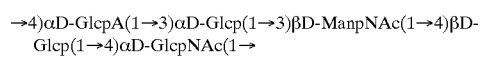

Type 9V:

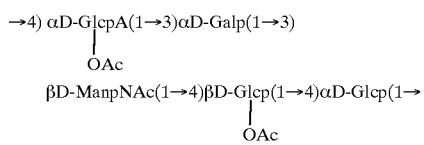

Type 10A:

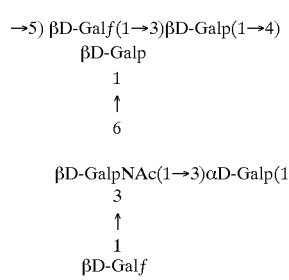

Type 11A:
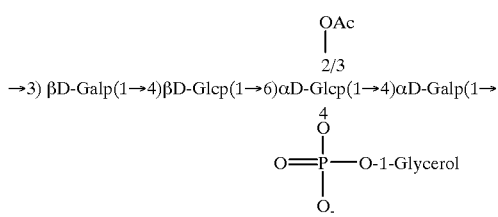
Type 12F:
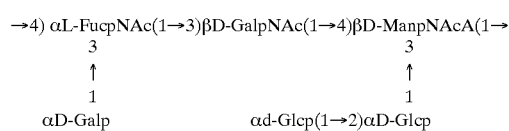
Type 14:
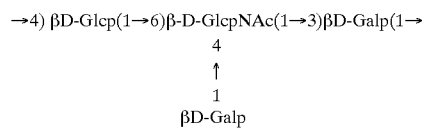
Type 15B:
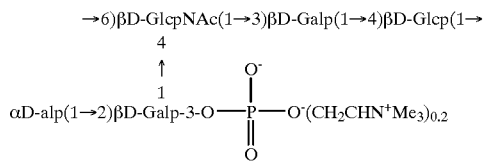
Type 17F:
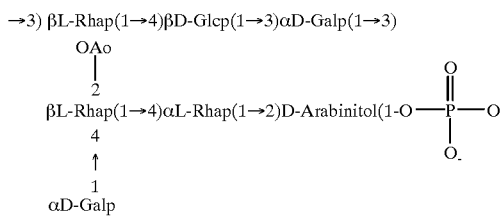
Type 18C:
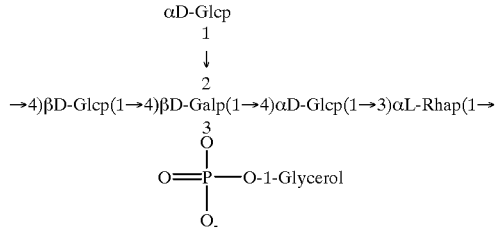
Type 19A:
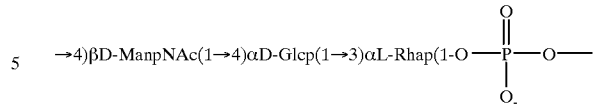
Type 19F:
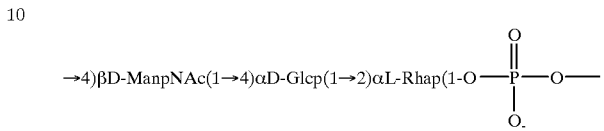
Type 20:
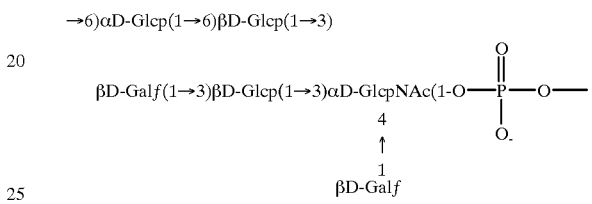
Type 22F:
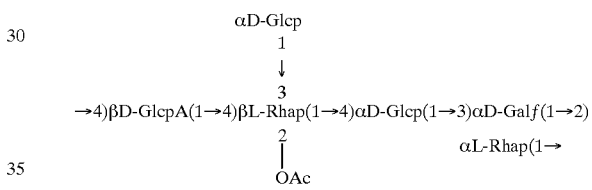
Type 23F:
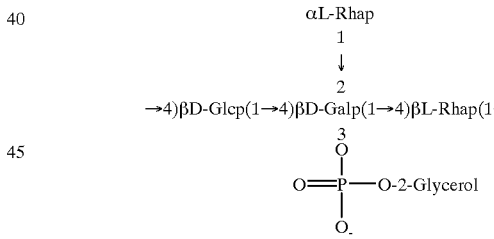
Type 25F:
  Not reported
Type 33F:
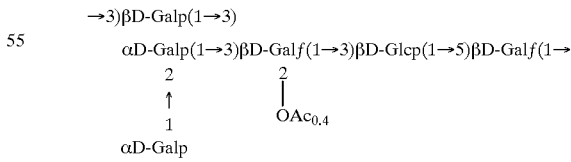
In the above listing of capsular polysaccharide structures, AAT=2-acetamido-4-amino-2,4,6-trideoxy-D-galactose; Sug=2-acetamido-2,6-dideoxy-D-xylo-hexos-4-ulose (ref. 27).
In particular, a capsular polysaccharide which corresponds to that isolatable from the *Streptococcus pneumoniae* strain Pn14 or Pn6B may provide the capsular polysaccharide employed herein.

The novel conjugate molecules provided herein may be components in immunogenic compositions. Accordingly, another aspect the present invention provides an immunogenic composition comprising an immuno-effective amount of a conjugate molecule as defined above. Such immunogenic composition may be formulated as a vaccine for in vivo administration to a host, which may be a primate, particularly a human host, to confer protection against disease caused by the Streptococcus strain, particularly a *Streptococcus pneumoniae* strain. The vaccine may also confer protection against disease caused by the Haemophilus strain, particularly a *Haemophilus influenzae* strain. The outer membrane protein of the *Haemophilus influenzae* strain particularly may be the P1, P2 or P6 outer membrane protein.

The immunogenic composition may comprise at least one other immunogenic or immunostimulating material, which may comprise at least one adjuvant. Such an adjuvant may comprise aluminum phosphate, aluminum hydroxide, QS21, calcium phosphate, calcium hydroxide, zinc hydroxide, a glycolipid analog, an octadecyl tyrosine ester of an amino acid, or a lipoprotein.

The present invention further provides a method of generating an immune response in a host by administering thereto an immuno-effective amount of the immunogenic composition defined above. The immune response obtained may provide protection to the host against disease caused by the Streptococcus strain and preferably also provides protection to the host against disease caused by the Haemophilus strain.

The novel conjugate molecule as well as antibodies thereto also are useful in diagnostic procedures and diagnostic kits. Accordingly, the present invention additionally provides a method of determining the presence of antibodies specifically reactive with a capsular polysaccharide of a Streptococcus strain in a sample, comprising the steps of:

(a) contacting the sample with the conjugate molecule provided herein to produce complexes comprising the conjugate molecule and any antibodies present in the sample specifically reactive therewith; and (b) determining the production of the complexes.

In addition, the present invention provides a method of determining the presence of a capsular polysaccharide of a Streptococcus strain in a sample, comprising the steps of:

(a) immunizing a subject with the immunogenic composition provided herein to produce antibodies specific for the capsular polysaccharide;

(b) contacting the sample with the antibodies to produce complexes comprising any capsular polysaccharide of a Streptococcus strain present in the sample and the capsular polysaccharide specific antibodies; and (c) determining production of the complexes.

The present invention further provides a method of determining the presence of antibodies specifically reactive with an outer membrane protein of a Haemophilus strain in a sample, comprising the steps of:

(a) contacting the sample with a conjugate of claim 1 to produce complexes comprising the conjugate molecule and any said antibodies present in the sample specifically reactive therewith; and (b) determining production of the complexes.

The present invention, in yet a further embodiment, provides a method of determining the presence of an outer membrane protein of a Haemophilus strain in a sample, comprising the steps of:

(a) immunizing a subject with an immunogenic composition provided herein to produce antibodies specific for the outer membrane protein;

(b) contacting the sample with the antibodies to produce complexes comprising any outer membrane protein of a Haemophilus strain present in the sample and the outer membrane specific antibodies; and (c) determining production of the complexes.

Furthermore, the present invention provides a diagnostic kit for determining the presence of antibodies in a sample specifically reactive with a capsular polysaccharide of a Streptococcus strain, comprising:

(a) the conjugate molecule provided herein;

(b) means for contacting the conjugate molecule with the sample to produce complexes comprising the conjugate molecule and any such antibodies present in the sample; and (c) means for determining production of the complexes.

In an additional aspect of the invention, there is provided a diagnostic kit for detecting the presence of a capsular polysaccharide of a Streptococcus strain in a sample, comprising:

(a) a capsular polysaccharide specific antibody to the immunogenic composition provided herein;

(b) means for contacting the antibody with the sample to produce a complex comprising the capsular polysaccharide and the antibody; and (c) means for determining production of the complex.

Additionally, the present invention provides a diagnostic kit for determining the presence of antibodies in a sample specifically reactive with an outer membrane protein of a Haemophilus strain, comprising:

(a) the conjugate molecule of claim 1;

(b) means for contacting the conjugate molecule with the sample to produce complexes comprising the conjugate molecule and any said antibodies present in the sample; and (c) means of determining the production of the complexes.

The present invention further provides a diagnostic kit for detecting the presence of an outer membrane protein of a Haemophilus strain in a sample, comprising:

(a) an outer membrane specific antibody to the immunogenic composition provided herein;

(b) means for contacting the antibody with the sample to produce a complex comprising the outer membrane protein and the antibody; and (c) means for determining production of the complex.

An additional aspect of the invention provides a process for individually isolating the P1, P2 and P6 outer membrane proteins for a Haemophilus strain, in purified form, comprising the steps of:

(a) providing a cell paste of the Haemophilus strain;

(b) selectively extracting P2 protein from the cell paste to produce a first supernatant containing said P2 protein substantially free from P1 and P6 protein and a residual precipitate containing P1 and P6 protein;

(c) separating the first supernatant from said residual precipitate;

(d) concentrating the P2 protein in said first supernatant to produce a second supernatant;

(e) purifying P2 protein in said second supernatant substantially free from pyrogens, lipopolysaccharides and other impurities solubilized from said paste by said selective extraction step;

(f) selectively extracting P1 protein from the residual precipitate from step (b) to produce a third supernatant containing P1 protein and a P6-containing precipitate;

(g) separating said third supernatant from said P6-containing precipitate;

(h) concentrating the P1 protein in said third supernatant to produce a fourth supernatant;

(i) purifying P1 protein in said fourth supernatant substantially free from pyrogens, lipopolysaccharides, P2 protein and other impurities solubilized step in step (f);

(j) selectively extracting the P6-containing precipitate to produce a P6-containing supernatant and a first extracted precipitate;

(k) separating said P6-containing supernatant from said first extracted precipitate;

(l) concentrating the P6 protein in said P6-containing supernatant to produce a fifth supernatant; and (m) purifying P6 protein in said fifth supernatant substantially free from pyrogens, lipopolysaccharides, P1 protein and other impurities solubilized step in step (j).

The selective extraction of the P2 protein from the cell paste may be effected using an aqueous sodium chloride solution of about 0.2 to about 2M. Concentration of the P2 protein in the first supernatant may be effected by precipitation of the P2 protein from the first supernatant, separation of the precipitated P2 protein, resolubilization of the P2 protein by selective detergent extraction while leaving a second extracted precipitate containing contaminants solubilized from the cell paste, and separation of the crude P2 extract (second supernatant).

The Haemophilus strain which is processed and according to this aspect of the invention may be *Haemophilus influenzae* type b, in which case the supernatant remaining from separation of the precipitated P2 protein contains polyribosylphosphate (PRP), and such PRP may be recovered and purified from that supernatant.

The purification step effected on the P2 protein may comprise selective removal of pyrogens from the P2-containing precipitate prior to the resolubilization step. This purification step also may include binding P2 protein in the crude P2 extract (second supernatant) to a first chromatographic column, which may be a hydroxyapatite matrix, selectively eluting contaminants including pyrogens and LPS from the first chromatographic column while leaving P2 protein bound to the column, and subsequently eluting purified P2 protein from the first chromatographic column.

The selective extraction of P1 protein from the residual P1-and P6-containing precipitate may be effected by detergent extraction. Concentration of the P1 protein may comprise selective precipitation of P1 protein from the third supernatant to form a P1-containing precipitate and resolubilization of the P1-containing precipitate after separation from the resulting seventh supernatant to obtain a crude P1 extract (fourth supernatant).

The purification step effected on the P1 protein may include binding the P1 protein and the contaminating P2 protein in the crude P1 extract to a second chromatographic column, which may be a DEAE-Sephacel matrix, selectively eluting the P1 protein from the second chromatographic column while leaving contaminating P2 protein bound to the column to provide an eluate, binding P1 protein in the eluate from the second chromatographic column to a third chromatographic column, which may be a hydroxyapatite matrix, selectively eluting contaminants including pyrogens and LPS from the third chromatographic column while leaving P1 protein bound to the column, and subsequently eluting purified P1 protein from the third chromatographic column. P1 protein in the eluate from the second chromatographic column may be concentrated prior to binding the P1 protein to the third chromatographic column.

The selective extraction of P6 protein from the P6-containing precipitate is generally effected by detergent extraction at an elevated temperature of about 40° C. to about 70° C. owing to the limited solubility of this protein at ambient temperatures. The concentration of P6 protein may be effected by selective precipitation of P6 protein from the P6-containing supernatant to form a P6-containing precipitate and an eighth supernatant from which the P6-containing precipitate is separated, and resolubilisation of the P6-protein by detergent extraction of the P6-containing precipitate to obtain a crude P6 extract (fifth supernatant).

Purification of the crude P6 extract may include binding P6 protein and P1 protein contaminants in the crude P6 extract to a fourth chromatographic column, which may be a DEAE-Sephacel matrix, selectively eluting the P6 protein from the fourth chromatographic column while leaving this P1 protein bound to the column to provide an eluate, binding P6 protein in the eluate from the fourth chromatographic column to a fifth chromatographic column, which may be a hydroxyapatite matrix, selectively eluting contaminants including pyrogens and LPS from the fifth chromatographic column while leaving P6 protein bound to the column, and subsequently eluting purified P6 protein from this fifth chromatographic column. The P6 protein in the eluate from the fourth chromatographic column may be concentrated prior to binding the P6 protein to the fifth chromatographic column.

Advantages of the present invention include the ability to obtain an enhanced immune response to capsular polysaccharides of Streptococcus strains without the necessity to employ carrier proteins which may because of their common-place use as immunogens, induce a hyper-immune response. Additionally, an immune response to the outer membrane protein of the Haemophilus strain also is achieved, providing from the same conjugate molecule, an immune response to two bacterial species which are causative agents of otitis media and other diseases.

BRIEF DESCRIPTION OF THE DRAWINGS

The present invention will be further understood from the following detailed description and Examples with reference to the accompanying drawings, in which.

DETAILED DESCRIPTION OF THE INVENTION

In one aspect, the present invention provides novel techniques which can be employed for preparing essentially pure P1, P2 and P6 outer membrane proteins of Haemophilus. Any Haemophilus strain may be conveniently used to provide the isolated and purified outer membrane proteins as provided herein. Such Haemophilus strains are generally available from clinical sources and from bacterial culture collections.

Figure 1:
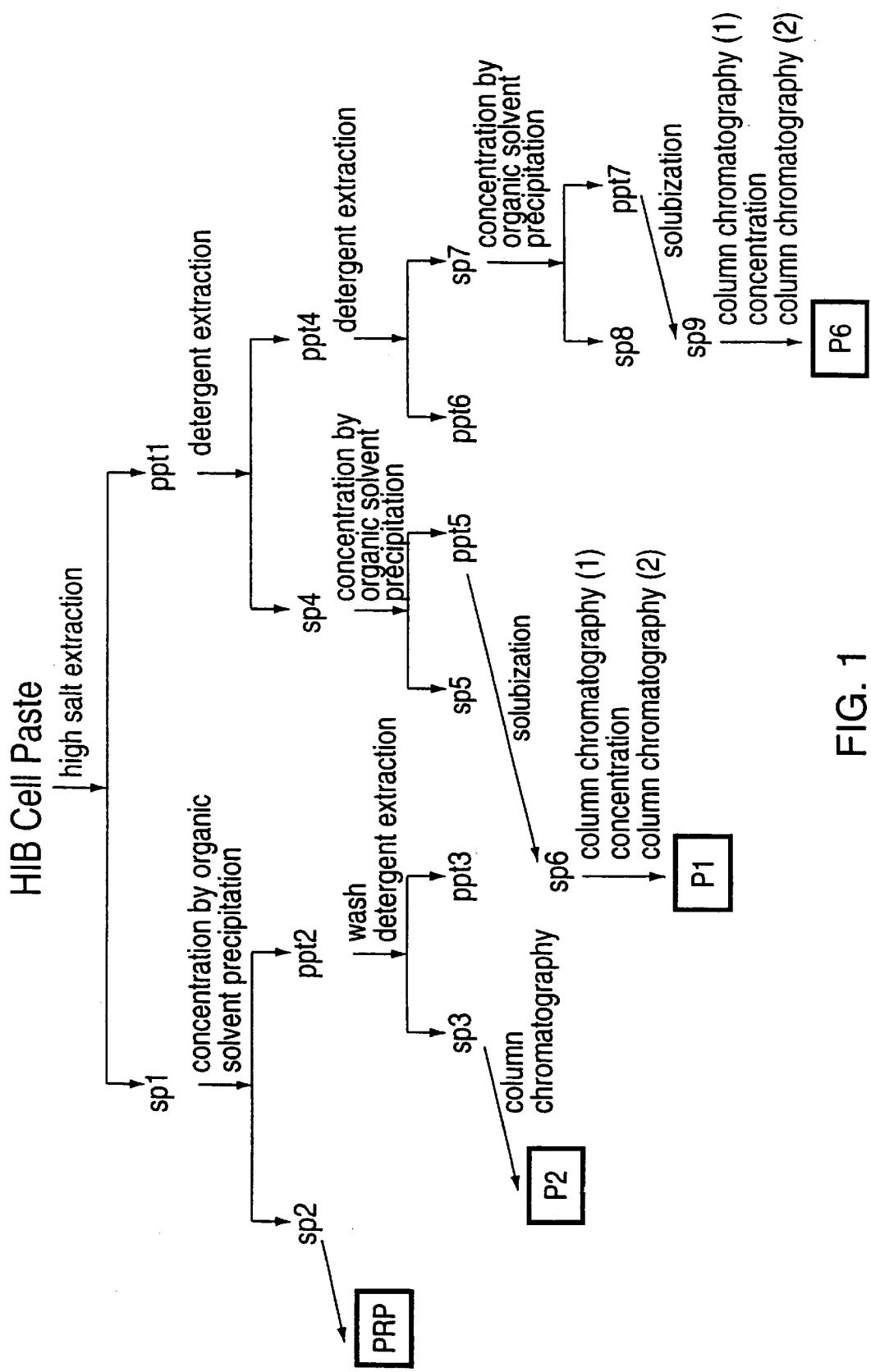
FIG. 1 is a schematic flow sheet of a procedure for the isolation of separately purified P1, P2 and P6 proteins of *Haemophilus influenzae* type b in accordance with one aspect of the present invention.

Referring to FIG. 1, there is illustrated a flow sheet of a method for individually isolating P1, P2 and P6 outer membrane protein from a Haemophilus strain.

As seen in FIG. 1, a Haemophilus cell paste containing the P1, P2 and P6 proteins, such as Hib cell paste, is extracted with, for example, NaCl at a concentration of between about 0.2 and 2M, to selectively extract P2 protein from the cell paste to produce a supernatant (SP1) containing P2 protein and substantially free from P1 and P6 proteins and a residual precipitate (PPT1) containing P1 and P6 protein. The P1- and P6-containing residual precipitate (PPT1) generally contains residual amounts of P2-protein. If the Haemophilus strain extracted is a *H. influenzae* type b strain, the supernatant containing P2 protein may contain polyribosylphosphate (PRP). The P2 protein in the supernatant (SP1) is selectively precipitated by a water-miscible organic solvent precipitation by, for example, adding ethanol to a final concentration of about 25%. The selective precipitation of the P2 protein (PPT2) in this way serves to concentrate the P2-containing supernatant for further processing.

Any PRP present in the P2-containing supernatant (SP2) remains in the aqueous phase and can be isolated from the supernatant produced by the P2 protein precipitation step, for example, as described in U.S. Pat. No. 4,496,538 (the disclosure of which is hereby incorporated by reference thereto). The P2-containing pellet (PPT2) is then washed with, for example, a urea, detergent containing buffer, such as, 50 mM Tris 2M urea/0.56 Triton X-100/0.2% DOC/150 mM NaCl pH 8.0, in order to remove pyrogens from the P2-containing pellet (PPT2). Any other convenient pyrogen removal procedure may be employed. The washed P2 containing pellet is then treated to selectively extract the P2 protein from the pellet and leave other -material solubilized in the initial paste extraction operation unsolubilized. Such selective extraction may be effected in any convenient manner, such as by selective detergent extraction, for example, by the use of octyl-glucoside (OG). Such octyl-glucoside extraction may be effected using 50 mM Tris/l% octyl-glucoside (OG)/0.2% DOC/150 mM NaCl under buffer conditions, such as, about pH 8.0 and may be performed at about 4° C. for at least one hour. Impurities remain in the unsolubilized precipitate (PPT3) and the P2 protein is in the supernatant as a crude P2 extract (SP3).

Further purification of P2 protein from the crude P2 extract (SP3) to remove lipopolysaccharides and further pyrogens may be effected by any convenient means including column chromatography on, for example, a hydroxyapatite matrix. Such chromatographic purification procedure may involve loading the crude P2 extract (SP3) onto a hydroxyapatite column, washing of the column to remove the impurities and then eluting the purified P2 protein under suitable pH conditions, generally about pH 7 to about pH 8.5.

P1 protein is selectively extracted from the residual precipitate (PPT1) from P2 extraction (FIG. 1) by, for example, at least one detergent extraction, such as, by using a buffered Triton X-100 solution. Residual P2 protein present in the precipitate also is extracted by this detergent extraction. Such Triton X-100 may be used at a concentration of about 0.2 to about 2 wt %, for example, about 0.5%, at a pH of about 7 to about 8.5, for example, about 8.0. The detergent extracted solution may be buffered to the desired pH in any convenient manner, for example, by employing about 10 to about 100 mM of Tris and about 2 to about 20 wt % EDTA. Following such selective extraction, there is produced a P1-containing supernatant (SP4) and a P6-containing precipitate (PPT4).

P1 protein is selectively precipitated from SP4 by, for example, using an organic solvent such as ethanol at a final concentration of about 25%. This procedure serves to concentrate the P1 protein for further processing and produces a P1-containing precipitate (PPT5). Contaminants remaining in the supernatant (SP5) are discarded. The P1 protein in the P1-containing precipitate (PPT5) is then selectively extracted using, for example, a buffered detergent solution, such as, 50 mM Tris/0.15% deoxycholate (DOC), pH 8.0. The P1 protein is thereby released into a supernatant termed crude P1 extract (SP6).

The P1 protein may be further purified from the crude P1 extract (SP6) by, for example, column chromatography, including DEAE-Sephacel column chromatography and hydroxyapatite chromatography. The DEAE-Sephacel column chromatography, or other convenient chromatographic procedure, may be used to separate contaminating P2 protein from this P1 protein. This separation may be effected by first binding both P1 and P2 proteins to the column and selectively eluting the P1 protein from the column, leaving the P2 protein bound to the column.

Prior to further processing, the P1-containing eluate from the DEAE-Sephacel column may be concentrated by precipitation using a water-miscible organic solvent, such as ethanol, followed by resuspension and dissolution. The resulting concentrate then is processed to remove pyrogens and lipopolysaccharides (LPS) in the same manner as described above for the P2 protein. The concentrate may be loaded onto a hydroxyapatite column, such that the P2 protein binds thereto, this column is washed to remove the pyrogens and LPS and then the purified P1 protein is eluted from the column. The conditions described above for P2 purification are suitable for the P1 purification.

P6 protein is selectively extracted from the residual precipitate (PPT4) from the P1 extraction (FIG. 1) by, for example, selective detergent extraction. Such extraction may be effected with a buffered detergent solution, such as, 10 to 100 mM Tris/0.1 to 0.2% DOC at a pH of about 7 to about 8.5. In general, elevated temperatures are required to effect extraction of the P6 protein from PPT4 and temperatures of about 40° C. to about 70° C. may be employed. This selective extraction produces a P6-containing supernatant SP7 and a precipitate (PPT6), which is discarded. P6 protein is selectively precipitated from the P6 containing supernatant (SP7) by a water-miscible organic solvent precipitation, such as by alcohol precipitation (including ethanol) at a final concentration of 25%. This selective precipitation serves to concentrate the P6 protein for further processing and produces a P6 containing precipitate (PPT7) and a supernatant SP8 which is discarded. Purified P6 protein may be obtained from the P6 containing precipitate PPT7 by selective extraction with a detergent mixture, such as 10 to 100 mM/Tris/0.1 to 0.2% DOC at a pH of about pH 7 to about pH 8.5 to produce a supernatant containing P6 protein (SP9) as a crude P6 extract.

P6 protein may be further purified from the crude P6 extract SP9 by column chromatography, such as, DEAE-Sephacel column chromatography and hydroxyapatite chromatography. The DEAE-Sephacel column chromatography, or other convenient chromatographic procedure, may be used to separate contaminating P1 protein from SP9. This separation may be effected by first binding both P6 and P1 proteins in SP9 to the column and selectively eluting the P6 protein from the column, leaving the P1 protein bound to the column.

Prior to further processing, the P6-containing eluate may be -concentrated by precipitation using a water-miscible organic solvent, such as ethanol, followed by resuspension and dissolution. The resulting concentrate then is processed to remove pyrogens and LPS in the same manner as described above for the P2 and P1 proteins. The concentrate may be loaded onto a hydroxyapatite column, such that the P6 protein binds to the column, the column is washed to remove pyrogens and LPS and then the purified P6 protein is eluted from the column. The conditions described above for P2 purification are suitable for the P6 purification.

Figure 2:
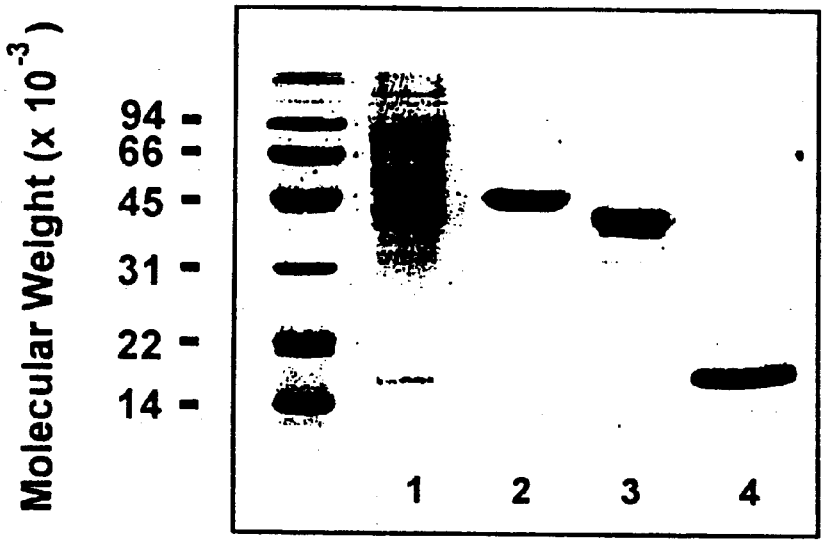
FIG. 2 shows an analysis of cell paste and purified P1, P2 and P6 by SDS-PAGE. Lane 1=Hib cell paste, Lane 2=P1 protein, Lane 3=P2 protein and Lane 4=P6 protein, mwt are molecular weight size markers 97.4, 66.2, 45.0, 31.0, 21.5 and 14.4 kDa respectively.

Referring to FIG. 2, there is shown an SDS-PAGE analysis of purified P1 (Lane 2), P2 (Lane 3) and P6 (Lane 4), purified according to the procedure described above with respect to FIG. 1. The outer membrane proteins P1, P2 and P6 are at least 70% pure and purities of 95% can readily be achieved. Purified proteins are non-pyrogenic as shown by the pyrogenicity data shown in Table 2 (below).

As described above, the present invention is particularly concerned with the provision of immunogenic conjugate molecules which comprise at least a portion of a capsular polysaccharide of a Streptococcus strain linked to at least a portion of an outer membrane protein of a Haemophilus strain. The capsular polysaccharide and the outer membrane protein, or selected portions thereof, may be linked directly or through a linking molecule. The selected portion of the capsular polysaccharide and of the outer membrane protein, when employed, provide, in the conjugate molecule, an enhanced immune response to the capsular polysaccharide. In particular embodiments of the invention, there is provided an immunogenic conjugate molecule comprising the P6 outer membrane protein of *H. influenzae* linked to the capsular polysaccharides Pn14 and Pn6B of *Streptococcus pneumoniae*. These particular and other capsular polysaccharides and the P6 protein have been described in detail above.

Figure 3:
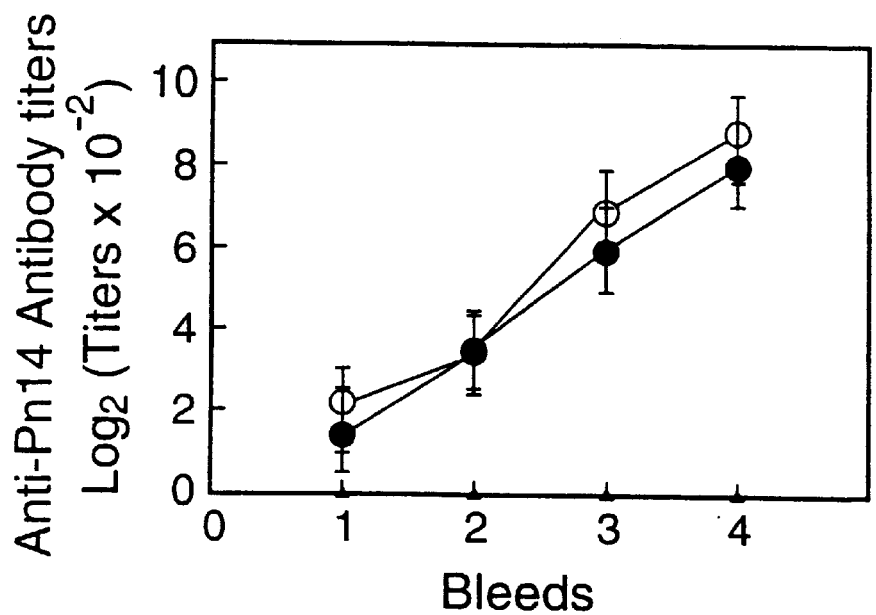
FIG. 3 shows the kinetics of anti-Pn14 antibody responses. Pn14-P6 conjugate was produced by the direct conjugation method described below. Groups of five Balb/c mice were injected three times s.c. with 15 μg of either Pn14 CP alone (▲) or Pn14-P6 conjugate in the presence (●) or absence (○) of $AlPO_4$ (1.5 mg per dose) on days 1, 35 and 48. Blood samples were collected on days 21 34, 47 and 60, as indicated by bleeds 1, 2, 3 and 4, respectively. Anti-Pn14 antibody titers were measured by EIAs. Each bar represents the antibody titers from five animal sera tested individually ± one SD.
Figure 4:
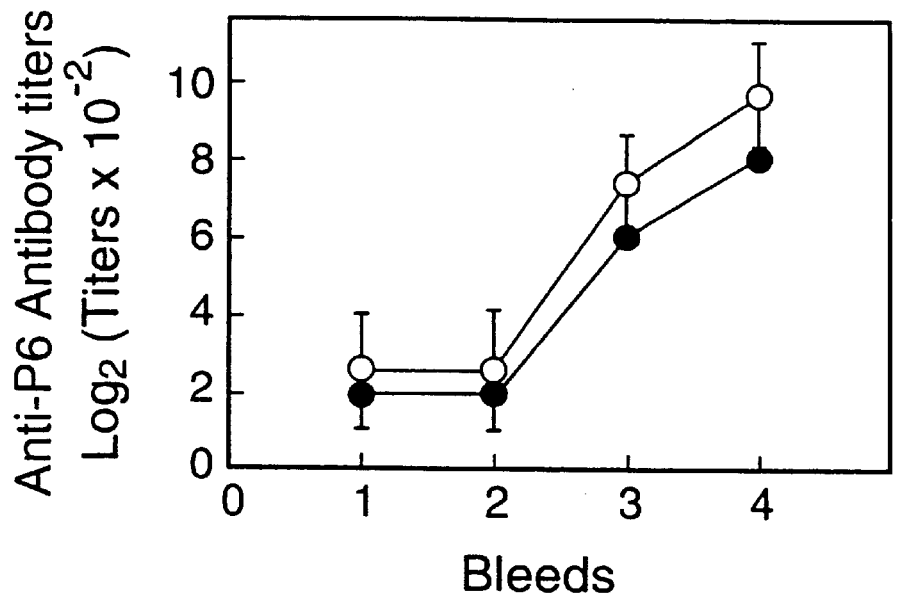
FIG. 4 shows the kinetics of anti-P6 antibody responses induced by Pn14-P6 conjugate in the presence (●) or absence (○) of $AlPO_4$, following the procedure described above for FIG. 3.

Referring to FIGS. 3 and 4 and Table 1 (below), there is illustrated the immunogenicity of the conjugate molecules. In FIG. 3, there is shown the kinetics of anti-Pn14 antibody responses elicited by either free Pn14 CP (▲) or Pn14-P6 conjugate, provided in accordance with the invention, in the presence (●) or absence (○) of $AlPO_4$ (1.5 mg per dose). Pn14-P6 conjugate induced significantly higher antibody response to Pn14 CP irrespective to the presence of $AlPO_4$, whereas free polysaccharide did not elicit any anti-Pn14 antibodies in mice. FIG. 4 shows the kinetics of anti-P6 antibody response in mice produced by immunization with Pn14-P6 conjugate in the presence (●) or absence (○) of $AlPO_4$ (1.5 mg per dose). Similar to the anti-Pn14 antibody response, Pn14-P6 conjugate induced high titres of anti-P6 IgG in mice by day 47 (bleed 3) and day 60 (bleed 4). The difference in the mean anti-P6 antibody titres between the two groups (with and without $AlPO_4$) of final bleed sera is not statistically significant (p=0.736).

Figure 5:
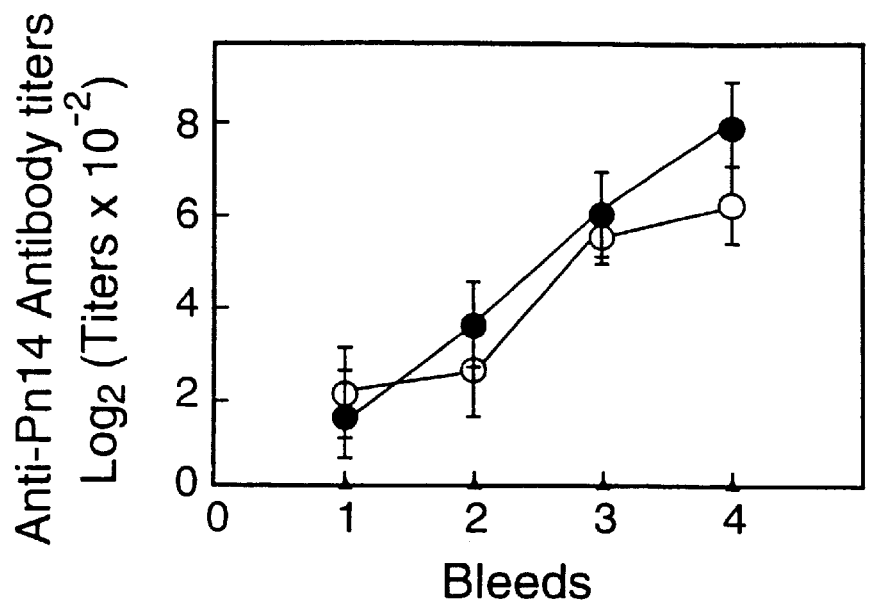
FIG. 5 illustrates the comparative analysis of anti-Pn14 antibody responses induced by free Pn14 (▲), Pn14-P6 conjugates produced by either a direct (●) or an indirect (○) conjugation method. Groups of five Balb/c mice were immunized three times s.c. with 15 μg of either Pn14 CP alone (▲), or Pn14-P6 conjugates in the presence of $AlPO_4$. Blood sampling and the measurements were made as described above for FIG. 3. Blood samples were analyzed for anti-Pn14 antibody titers by EIAs as described above-for FIG. 3.

FIG. 5 illustrates the comparative analysis of anti-Pn14 antibody responses induced by Pn14-P6 conjugates produced by either a direct (●) or an indirect (○) conjugation method. Immunization of mice was performed the same way as in FIG. 3 above in the presence of $AlPO_4$ (1.5 mg per dose). Both conjugates elicited significantly higher IgG titres to Pn14 CP than that of free Pn14 CP (▲). The mean anti-Pn14 CP antibody titres induced by both conjugates were not statistically significant at the 0.01 level (p=0.035).

Figure 6:
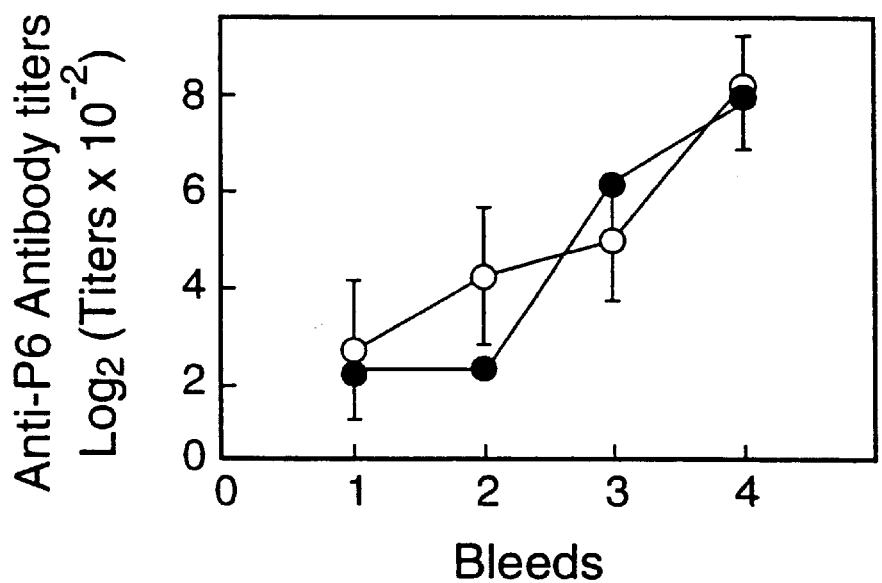
FIG. 6 illustrates the comparative analysis of anti-P6 antibody response induced by Pn14-P6 conjugates produced by either a direct (●) or an indirect (○) conjugation method, following the procedure described above for FIG. 5.

FIG. 6 illustrates the comparative analysis of anti-P6 antibody response induced by Pn14-P6 conjugates produced by either a direct (●) or an indirect (○) conjugation method. Similar to the anti-Pn14 antibody response in FIG. 5 above, the mean anti-P6 antibody titres in the final bleed induced by both conjugates were not statistically significant (p=0.724).

The results shown in Table 1, illustrate the anti-Pn6B and anti-P6 antibody responses in mice produced by immunization with either P6 protein or Pn6B-B6 conjugate, provided in accordance with the invention, in the presence or absence of $AlPO_4$ (1.5 mg per dose). Immunization with free Pn6B CP did not elicit any noticeable anti-Pn6B IgG irrespective of the presence or absence of $AlPO_4$. In contrast, immunization with Pn6B-P6 conjugate raised anti-Pn6B IgG antibodies in mice either with or without $AlPO_4$. The mean anti-Pn6B or anti-P6 IgG titres induced by immunization the Pn6B-P6 conjugate with or without $AlPO_4$ were not statistically significant (p=0.252 and p=0.806 for anti-Pn6B and anti-P6 IgG titres, respectively).

Figure 7:
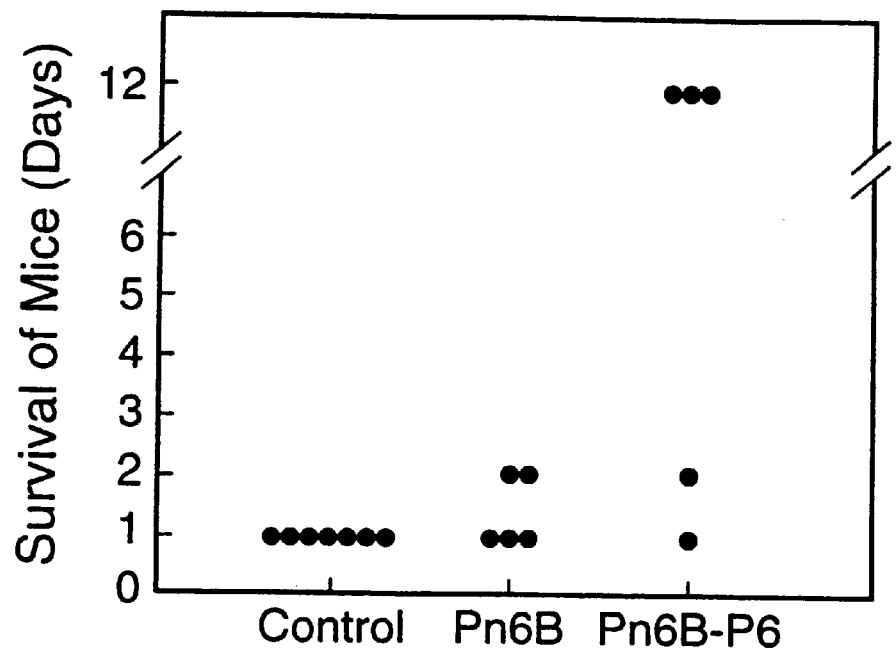
FIG. 7 shows the protective ability of Pn6B-P6 conjugate against *S. pneumoniae* challenge in a mouse active protection model in comparison to Pn6B alone. Groups of five to eight mice were immunized three times s.c. with 15 μg of indicated antigens in the presence of $AlPO_4$ (1.5 mg per dose) on days 1, 35 and 48. Blood samples were collected on day 60. Mice were inoculated i.p. with 15,000 cfu of *S. penumoniae* strain 6 on day 61. Resultant deaths of mice were recorded daily up to 12 days.

Referring to FIG. 7, there is shown the protective ability of Pn6B-P6 conjugate, against *S. pneumoniae* challenge in a mouse active protection model. All seven mice in the immunized control group died after 24 hours. The longest survival time for mice immunized with free Pn6B CP was 48 hours. In contrast, three out of five mice immunized with Pn6B-P6 conjugate, provided according to the invention, were still alive and well up to 12 days post-challenge.

Figure 8:
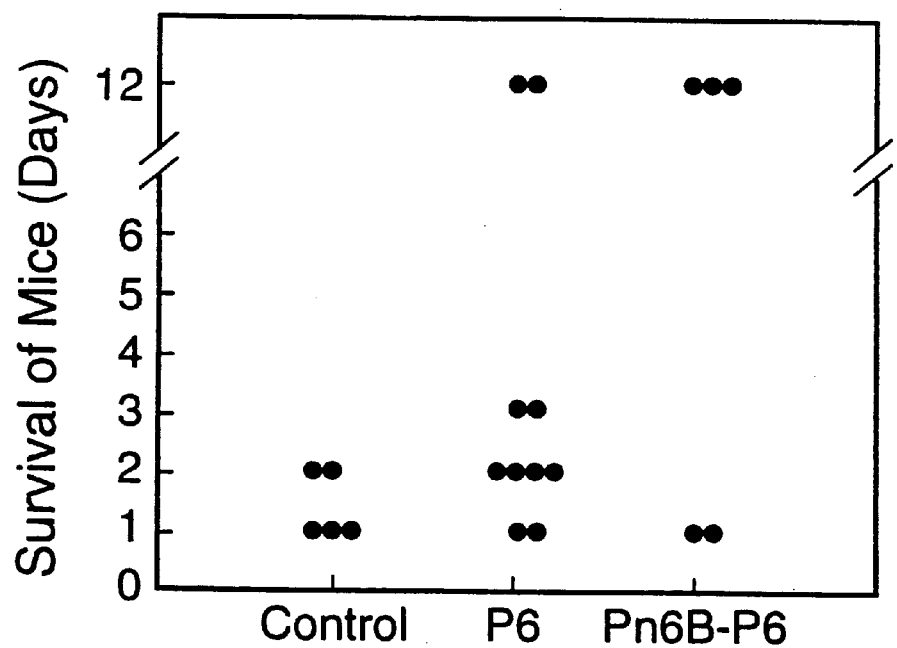
FIG. 8 illustrates the protection of mice against *H. influenzae* challenge by immunization with either P6 protein alone or Pn6B-P6 conjugate. Mice were immunized three times s.c. with 15 μg of either purified P6 protein or Pn6B-P6 conjugate in the presence of $AlPO_4$ (1.5 mg per dose) as described in FIG. 3. On day 61 mice were inoculated i.p. with 10,000 cfu of *H. influenzae* strain 66 in the presence of enhancement factors, mucin and haemoglobin as described by Brodeur et al (ref. 29). Resultant deaths of mice were recorded daily up to 12 days.

FIG. 8 illustrates the protection of mice against *H. influenzae* by immunization with either P6 protein alone or Pn6B-P6 conjugate. All five mice in the immunized control group died 48 hours after challenge. In the P6-immunized group, two mice survived for three days and another two mice were alive and well up to 12 days post challenge. For the animals immunized with Pn6B-P6 conjugate, provided according to the invention, three out of five mice survived and were healthy up to 12 days post challenge.

It is clearly apparent to one skilled in the art, that the various embodiments of the present invention have many applications in the fields of vaccination, diagnosis, treatment of, for example, Streptococcus and Haemophilus infections, and the generation of immunological reagents. A further non-limiting discussion of such uses is further presented below.

1. Vaccine Preparation and Use

Immunogenic compositions, suitable to be used as vaccines, may be prepared from the conjugate molecule as disclosed herein. The vaccine elicits an immune response in a subject which produces antibodies, including anti-capsular polysaccharide and anti-outer membrane protein antibodies and antibodies that are opsonizing or bactericidal. Should the vaccinated subject be challenged by the bacterium from which the capsular polysaccharide was derived for example, the Streptococcus strain and/or a Haemophilus strain, such antibodies bind to and inactivate the bacteria. Furthermore, opsonizing or bactericidal antibodies may also provide protection by alternative mechanisms.

Immunogenic compositions including vaccines may be prepared as injectables, as liquid solutions or emulsions. The conjugate molecule may be mixed with pharmaceutically acceptable excipients which are compatible with the conjugate molecule. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions provided according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration, including suppositories and oral formulations, may be desirable. For suppositories, binders and carriers may include, for example, polyalkalene glycols or triglycerides. Oral formulations may include normally employed incipients, such as, for example, pharmaceutical grades of saccharine, cellulose and magnesium carbonate. These compositions can take the form of solutions, suspensions, tablets, pills, capsules, sustained release formulations or powders and contain about 1 to about 95% of the conjugate molecules. The immunogenic preparations and vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner. However, suitable dosage ranges are readily determinable by one skilled in the art and may be of the order of micrograms of the conjugate molecule. Suitable regimes for initial administration and booster doses are also variable, but may include an initial administration followed by subsequent administrations. The dosage may also depend on the route of administration and will vary according to the size of the host.

The concentration of the conjugate molecule in an immunogenic composition according to the invention is in general about 1 to about 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes;
(5) synergy with other adjuvants;
(6) capability of selectively interacting with populations of antigen presenting cells (APC);
(7) ability to specifically elicit appropriate TH1 or TH2 cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 23) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. (ref. 24), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller (ref. 25) describes a peptide with a sequence homologous to a foot-and-mouth disease viral protein coupled to an adjuvant tripalmityl-S-glyceryl-cysteinylserylserine, being a synthetic analogue of the N-terminal part of the lipoprotein from Gram negative bacteria. Furthermore, Deres et al. (ref. 26) reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-S-[2,3-bis(palmitylxy)-(2RS)-propyl-[R)-cysteine (TPC).

2. Immiunoassays

The conjugate molecules of the present invention are useful as immunogens for the generation of antibodies to the capsular polysaccharide and/or the outer membrane protein, as an antigen in immunoassays including enzyme-linked immunosorbent assays (ELISA), RIAs and other non-enzyme linked antibody binding assays or procedures known in the art for the detection of antibodies. In ELISA assays, the conjugate molecule is immobilized onto a selected surface, for example, a surface capable of binding proteins, such as, the wells of a polystyrene microtiter plate. After washing to remove incompletely adsorbed conjugate molecule, a nonspecific protein, such as, a solution of bovine serum albumin (BSA), that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures, such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound conjugate molecule, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

EXAMPLES

The above disclosure generally describes the present invention. A more complete understanding can be obtained by reference to the following specific Examples. These Examples are described solely for the purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Methods of protein biochemistry, carbohydrate chemistry and immunology used but not explicitly described in this disclosure and these Examples are amply reported in the scientific literature and are well within the ability of those skilled in the art.

Example 1

This Example illustrates the growth of *Haemophilus influenzae*.

Hib strain Eagan was grown to high cell density in brain heart infusion (BHI) broth (Difco Laboratories, Detroit, Mich.), supplemented with hemin and nicotinamide adenine dinucleotide (NAD) both at 2 μg per ml. Hib cells were precipitated by adding 10% cetavalon to the growth medium to a final concentration of 0.1%. Hib cells were harvested by centrifugation at 10,000 g for 20 min, to collect Hib cell paste.

Example 2

This Example illustrates a process for individually isolating P1, P2 and P6 outer membrane protein from a Haemophilus strain.

The *H. influenzae* cell paste from Example 1 was resuspended in 0.4 M NaCl (20 ml per 1 g of cell paste) at 5% (w/v). The cells were homogenized with a Polytron homogenizer for 3 to 5 minutes and the suspension stirred at room temperature for 2 hr. The suspension was then centrifuged at 8,000 g for 30 min. The supernatant SP1 was used for purifying P2 and PRP.

To separate PRP from P2, ethanol was added to SP1 to a final concentration of 25% and the mixture incubated at room temperature for 1 hour, and then centrifuged at 20,000 g for 30 min. PRP was present in the supernatant SP2 and the pellet PPT2 contained the majority of P2. The pellet was washed by resuspending in 50 mM Tris/2M Urea/0.5% Triton X-100/0.2% DOC/150 mM NaCl (pH 8.0) at a ratio of 1 ml of buffer to 1 g of original cell paste wet weight. The mixture was centrifuged at 20,000 g for 30 min. The resulting supernatant was discarded and the pellet was washed again as described above. The pellet after the second wash was resuspended in 50 mM Tris/1% octyl-glucoside (OG)/0.2% DOC/150 mM NaCl (pH 8.0) at a ratio of 1 ml of buffer to 1 g of original cell paste. The solution was stirred at 4° C. for at least 1 hr and then centrifuged at 20,000 g for 30 min. The resulting supernatant was called "P2 crude extract" (SP3).

The P2 protein was purified from the crude P2 extract by hydroxyapatite (HTP) chromatography. A HTP column was prepared using 1 ml of HTP matrix for every 3 ml of P2 crude extract, HTP was equilibrated with 50 mM Tris (pH 8.0). The P2 crude extract was diluted 10 fold with 50 mM Tris/0.5% Triton X-100/0.1% DOC/150 mM NaCl (pH 8.0) to reduce the final concentration of OG to less than 0.1%. The solution was then stirred at between 4 and 20° C. for 1 hr. The above suspension was loaded onto the HTP column. The column was washed with 10 column volumes of each of the following buffers: 50 mM Tris (pH 8.0); 50 mM Tris/0.5% Triton X-100/0.2% DOC/150 mM NaCl (pH 8.0); and then 50 mM Tris (pH 8.0). The column was then eluted with 10 column volumes of 50 mM Tris/2% OG/0.4% DOC/150 mM NaCl (pH 8.0) and fractions collected. The amount of P2 in the fractions was determined by BCA protein assay. The purity and pyrogenicity of P2 was assessed by SDS-PAGE followed by densitometry scanning, the rabbit pyrogen test and the LAL gelation test (FIG. 2 and Table 2). The purified P2 was stored at 4° C.

The residual precipitate (PPT1) was resuspended in 50 mM Tris/0.5% Triton X-100/10 MM EDTA (pH 8.0) at 10 ml of buffer per 1 g of precipitate. The suspension was stirred at 4°C. overnight and then centrifuged at 20,000 g for 30 min. This supernatant was saved and the pellet subjected to a second extraction with 50 mM Tris/0.5% Triton X-100/10 mM EDTA (pH 8.0) at 10 ml of buffer per 1 g of material (2 hr at room temperature). The pellet PPT4 was saved for P6 extraction. The two supernatants were combined to produce SP4 and ethanol was added to a final concentration of 25%. This solution was stirred at 4°C. overnight, and then centrifuged at 20,000 g for 30 minutes to collect the P1-containing precipitate (PPT5). The P1-containing precipitate was then resuspended in 50 mM Tris/0.15% sodium deoxylcholate (DOC) (pH 8.0) at 1 ml of buffer per 1 g of the residual precipitate. The above solution was centrifuged at 3,000 g for 10 min to remove insoluble material and the supernatant was termed "crude P1 extract" (SP6).

Purified P1 was obtained from the P1 crude extract SP6 by DEAE-Sephacel column chromatography. A DEAE-Sephacel column was prepared using 1 ml of DEAE-Sephacel matrix for every 8 to 10 ml of crude P1 extract and equilibrated with 50 mM Tris (pH 8.0). The crude P1 extract was loaded onto the DEAE-Sephacel column and both P1 and contaminating P2 bind to the column. The column was washed with 10 column volumes of 50 mM Tris/0.15% DOC/0.1% Triton X-100 (pH 8.0) and then washed with 10 column volumes of 50 mM Tris (pH 8.0). The P1 protein was eluted with 10 column volumes of 50 mM Tris/0.5% Triton X-100 (pH 8.0) and the P2 remains bound to the column under these conditions. The resulting P1-containing fraction was precipitated with ethanol (final concentration 25%) at 4° C. overnight and the precipitate harvested by centrifugation (20,000 g, 30 min). This precipitate was redissolved in 50 mM Tris/0.15% DOC (PH 8.0) with $\frac{1}{10}$ of the original volume. P1 in the P1-containing fraction was further purified by hydroxyapatite (HTP) column chromatography. A HTP column was prepared and equilibrated with 50 mM Tris (pH 8.0). The HTP column was washed with 20 column volumes of 50 mM Tris/0.5M urea/0.2% DOC/0.1% Triton X-100 (pH 8.0) and then washed with 20 column volumes of 50 mM Tris (pH 8.0). P1 was eluted with 14 column volumes of 50 mM Tris/0.5% Triton X-100/10 mM EDTA (pH 8.0) and fractions representing 2 column volumes (i.e. total 7 fractions) were collected. The amount of P1 in HTP fractions was determined by the BCA protein assay. The purity and pyrogenicity of P1 was assessed by SDS-polyacrylamide gel electrophoresis and LAL gelation tests, respectively (FIG. 2 and Table 2).

The P6-containing precipitate (PPT4) was extracted with 50 mM Tris/0.15% DOC (pH 8.0) at 5 ml of buffer per 1 g of cell paste wet weight. After stirring to break the precipitate, the mixture is left at 60 ° C. for 2 h and then centrifuged at 20,000 g for 30 min. The supernatant was saved and the pellet subjected to a second extraction using 50 mM Tris/0.15% DOC (pH 8.0) with half of the volume in the first extraction. The two P6-containing supernatants were combined to produce SP7 and ethanol added to a final concentration of 25%. After stirring at 4° C. overnight, the solution was centrifuged at 20,000 g for 30 min to collect the P6-containing precipitate (PPT7). The P6-containing precipitate was resuspended in 50 mM Tris/0.15% DOC (pH 8.0) at $\frac{1}{10}$ of the original volume. The solution was then centrifuged at 3,000 g for 10 min to remove insoluble material. The supernatant was termed "P6 crude extract" (SP9). The P6 crude extract was further purified by column chromatography. A DEAE-Sephacel column was prepared using 1 ml of DEAE-Sephacel matrix for every 3 ml of P6 crude extract) and equilibrated with 50 mM Tris (pH 8.0). The P6 crude extract was loaded onto the DEAE-Sephacel column. P6 as well as contaminating P1 bind to the column. The column was washed with 10 column volumes of 50 mM Tris/0.5% Triton X-100 (pH 8.0) to remove contaminating P1, followed by 10 column volumes of 50 mM Tris (pH 8.0). P6 was eluted with 6 to 7 column volumes of 50 mM Tris/0.5M NaCl (pH 8.0) and fractions representing 1 column volumes (i.e. total 6 to 7 fractions) were collected.

The resulting P6-containing fraction was further purified by hydroxyapatite chromatography. A HTP column was equilibrated with 50 mM Tris (pH 8.0). The P6-containing fraction was loaded directly onto the HTP column. The HTP column was washed with 10 column volumes of 50 mM Tris (pH 8.0). P6 protein was eluted with 8 column volumes of 50 mM Tris/0.2% Triton X-100/10 mM EDTA (pH 8.0) and collected. The amount of P6 in HTP fraction was determined by the BCA protein assay. The purity and pyrogenicity of P6 was assessed by SDS-PAGE followed by densitometry scanning, and the LAL assay, respectively (FIG. 2 and Table 2). The P6 obtained was concentrated by filtration using a PM-10 membrane and then stored at −20° C.

Example 3

This Example illustrates the purification of capsular polysaccharides from *Streptococcus pneumoniae*.

High molecular weight polysaccharide of *S. pneumoniae* may be purchased commercially from, for example, the American Type Culture Collection (Rockville, Md.). Alternatively the polysaccharide may be isolated by methods described in, for example, Porro et al 1983 (ref. 28) or as described in published European patent applications EP 477 508 and EP 534 764 each of which reference is incorporated herein by reference thereto.

Example 4

This Example illustrates the controlled periodate oxidation of polysaccharides.

Fifty mg of polysaccharides, prepared as described in Example 3, were dissolved in 4 ml of de-ionized water and were oxidized using 1 ml of 500 mM $NaIO_4$ in the dark at room temperature for 30 min. One ml of ethylene glycol was then added to the solution and the mixture was further stirred at room temperature for two hours. The oxidized oligosaccharides were dialysed against water, lyophilized, and used for conjugation to protein.

Example 5

This Example illustrates the synthesis of Pn14-P6 and Pn6B-P6 conjugates by an indirect conjugation method.

One mg of P6, prepared as described in Example 2, was dissolved in 2 ml of 150 mM phosphate buffer, pH 7.5. The solution was mixed with 13 mg of adipic acid dihydrazide and 14.5 mg of carbodiimide. The pH of the above mixture was adjusted to 4.8 using 1N HCl. The mixture was stirred at room temperature for two hours. The resulting ADH-P6 was purified by a Sephadex G-25 column using 150 mM phosphate buffer, pH 7.5. The protein peak was monitored by $A_{280}$. Oxidized polysaccharide Pn14 or Pn6B, prepared as described in Example 4, was coupled to ADH-P6 at a molar ratio of 2 to 1 at room temperature for six hours. After addition of 100 μg of cyanoborohydride, the reaction mixture was stirred at 37° C. for 5 days.

Example 6

This Example illustrates the synthesis of Pn14-P6 and Pn6B-P6 by a direct conjugation method.

Forty-five mg of oxidized Pn14 CP or Pn6B CP, prepared as described in Example 4, was dissolved in six ml of 150 mM phosphate buffer, pH 7.5, and then coupled to 1 mg of P6, prepared as described in Example 2, at a molar ratio of 15 to 1. After the addition of 100 μg of sodium cyanoborohydride for reductive amination, the mixture was stirred at 37° C. for 5 days.

Example 7

This Example illustrates the purification of conjugates.

The conjugates synthesized by either indirect or direct method, as described in Examples 5 and 6 above, were dialysed against water and then purified by a Sephadex G-100 column using 150 mM phosphate buffer, pH 7.5. The conjugate was eluted as the void volume and was collected, dialysed against water and stored at 4° C.

Example 8

This Example illustrates the analysis of polysaccharides and protein in conjugates.

Protein concentration was determined by the method of Bradford (ref. 17) with BSA as a standard. The carbohydrate content was assessed by the method of Dubois et al (ref. 18) after hydrolyzing the conjugate with 2 M trifluoroacetic acid at 80° C. for 6 hr. The purified respective polysaccharide was used as a standard. The ratio of protein to carbohydrate in the various conjugates is shown in Table 3.

Example 9

This Example illustrates the immunization of animals with either free polysaccharides or conjugates.

Groups of five Balb/c mice were injected subcutaneously (s.c.) on day 1 with a 15 μg dose (based on CP content) of the following purified antigens: Pn14 CP, Pn6B CP, Pn14-P6 or Pn6B-P6 conjugate, prepared as described in Examples 3 to 7, in the presence or absence of $AlPO_4$ (1.5 mg per dose). The animals received two booster injections on days 35 and 48 with the same antigen as the first injection. The blood samples were taken on days 21, 34, 47 and 60 for determining anti-Pn14, anti-Pn6B, and anti-P6 antibody titres by EIAs, as described in the following Example. The results are shown graphically in FIGS. 3 to 6.

Example 10

This Example illustrates the EIAs for determination of anti-pneumococcal CP antibodies in mouse sera as described by Panezutti et al. (ref. 19).

A conjugate of polysacharige linked to BSA was synthesized as described in Example 7. Microtiter wells were coated with 30/μg (based on CP content) of either Pn14-BSA or Pn6B-BSA conjugate for 16 hours at room temperature. The plates were then blocked with 0.1% (w/v) bovine serum albumin in PBS. The sera were serially diluted, added to the wells, then incubated for one hour at room temperature. Affinity-purified $F(ab')_2$ fragments of goat anti-mouse IgG (Fc specific) antibody conjugated to horseradish peroxidase were used as second antibody. The reactions were developed using tetramethylbenzidine ($TMB/H_2O_2$) and absorbencies was measured at 450 nm (using 540 nm as a reference wavelength) in a Flow Multiskan MCC microplate reader. The reactive titer of an antiserum was defined as the reciprocal of the dilution consistently showing a two-fold increase in absorbance over that obtained with the pre-bleed serum sample.

Example 11

This Example illustrates protection of mice against *S. pneumoniae* by immunogenic conjugate molecules.

Balb/c mice were immunized s.c. with either free Pn6B CP or Pn6B-P6 conjugate in the presence of $AlPO_4$ (1.5 mg per dose) on days 1, 35 and 48 as described above. On day 61, mice were challenged i.p. with 15,000 cfu of freshly grown *S. pneumoniae* strain 6. The subsequent death of mice was recorded daily up to 12 days. The data obtained is shown in FIG. 7. Mice immunized with conjugate were able to survive the challenge for at least 12 days.

Example 12

This Example illustrates the protection of mice against *H. influenzae* type b by immunogenic conjugate molecules.

Groups of five Balb/c mice were immunized s.c. with 15 μg of either purified P6 or Pn6B-P6 conjugate (based on CP content) absorbed with AlPO$_4$ on days 1, 35, and 48 as described above. On day 61, mice were challenged i.p. with 1,000 cfu of freshly grown *H. influenzae* strain 66 in the presence of enhancement factors, mucin and haemoglobin, as described by Broudeur et. al (ref. 29). The subsequent death of mice were recorded daily up to 12 days. The data obtained is shown in FIG. 8. Mice immunized with the conjugate were able to survive the challenge for at least 12 days.

SUMMARY OF THE DISCLOSURE

In summary of this disclosure, the present invention provides novel immunogenic conjugate molecules wherein the capsular polysaccharides of *Streptococcus pneumoniae* or other Streptococcus strain, or a portion thereof, was provided with enhanced immunogenicity by conjugation to an outer membrane protein of a Haemophilus strain, particularly the P6 protein of *Haemophilus influenzae*. A process for separately isolating and purifying P1, P2 and P6 outer membrane proteins of a Haemophilus strain also is provided. Modifications are possible within the scope of this invention.

TABLE 1

Anti-Pn6B and anti-P6 antibody responses in mice immunized with P6 and Pn6B-P6 conjugate

| Antigens | IgG titers[1] Log$_2$ (Titers × 10$^{-2}$) | |
|---|---|---|
| | To Pn6B | To P6 |
| Pn6B-P6 conjugate + AlPO$_4$ | 4.4 ± 1.6 | 9.2 ± 2.3 |
| Free Pn6B CP + AlPO$_4$ | <1.0 | 0 |
| Pn6B-P6 conjugate, no AlPO$_4$ | 3.6 ± 0.4 | 8.8 ± 2.7 |
| Free Pn6B CP, no AlPO$_4$ | <1.0 | 0 |
| P6 + AlPO$_4$ | 0 | 13.0 ± 0 |

[1]Balb/c mice were immunized three times (s.c.) with 15 μg of either P6 protein alone, or Pn6B CP alone, or Pn6B-P6 conjugate (produced by the indirect conjugation method) in the presence or absence of AlPO$_4$ (1.5 mg per dose) on days 1, 35 and 48. Blood samples were collected on day 60. Anti-Pn6B and anti-P6 antibody titers were analyzed by EIAs. Each value represents the mean antibody titer from five animal sera tested individually (± one standard deviation).

TABLE 2

Analysis of pyrogenicity in the purified P1, P2 and P6 fractions.

| Purified Protein | Dose Tested | Limulus Amebocyte Lysate Assay | Rabbit Pyrogen Test |
|---|---|---|---|
| P1 | 20 μg | Negative at 1 × 10$^{-3}$ to 10$^{-4}$ dilution | Negative |
| P2 | 20 μg | Negative at 1 × 10$^{-3}$ to 10$^{-4}$ dilution | Negative |
| P6 | 20 μg | Negative at 1 × 10$^{-4}$ dilution | Not tested |

TABLE 3

Analysis of the polysaccharide-protein conjugates.

| Conjugate | Molar Ratio of Protein:Carbohydrate |
|---|---|
| Pn14-P6 (direct) | 1:0.67 |
| Pn14-P6 (indirect) | 1:0.30 |

TABLE 3-continued

Analysis of the polysaccharide-protein conjugates.

| Conjugate | Molar Ratio of Protein:Carbohydrate |
|---|---|
| Pn6β-P6 (direct) | 1:0.12 |
| Pn6β-P6 (indirect) | 1:0.30 |

References

1. Austrian, R. 1987. Pneumococcal infections. In Harrison's Principles of Internal Medicine. 11th ed. E. Braunwald, K. J. Isselbacher, R. G. Petersdorf, J. D. Wilson, J. B. Martin, and A. S. Fauci (ed), McGraw-Hill, New York. 533–537.
2. Chommaitree, T., and V. M. Howie. 1987. Bacteriology of otitis media. p. 231–247. In J. Berstein and P. Ogra (ed.), Immunology of the ear. Reven Press, New York.
3. Giebink, G. S. 1989. The microbiology of otitis media. Pediatr. Infect. Dis. J. 8:518520.
4. Austrian, R. 1981. Some observations on the pneumococcus and on the current status of pneumococcal disease and its prevention. Rev. Infect. Dis. 3 (suppl):S1-S17.
5. Chu, C. Y., R. Schneerson, J. B. Robbins, and S. C. Rastogi. 1983. Further studies on the immunogenicity of *Haemophilus influenzae* type b and pneumococcal type 6A polysaccharide-protein conjugates. Infect. Immun. 40:245–256.
6. Schneerson, R., L. Levi, J. B. Robibin, D. M. Bryla, G. Schiffman, and T. Lagergard. 1992. Synthesis of a conjugate vaccine composed of pneumococcus type 14 capsular polysaccharide bound to pertussis toxin. Infect. Immun. 60:3528–3532.
7. Fattom, A., C. Lue, S. C. Szu, J. Mestecky, G. Schiffman, D. Bryla, W. F. Vann, D. Watson, J. B. Robbins, and R. Schneerson. 1990. Immune response in adult volunteers elicited by injection of the *Streptococcus pneumoniae* type 12F polysaccharide alone or conjugated to diphtheria toxoid. Infect. Immun. 58:2309–2312.
8. Robbins, J. B., R. Austrian, C.-J. Lee, S. C. Rastogi, G. Schiffman, J. Henrichsen, P. H. Makela, C. V. Broome, R. R. Facklam, R. H. Tiesjema, and J. C. Parke, Jr. 1983. Considerations for formulating the second-generation pneumococcal capsular polysaccharide vaccine with emphasis on the cross-reactive types within groups. J. Infect. Dis. 148: 1136–1159.
9. Shapiro, E. D., A. T. Berg, R. Austrian, D. Schroeder, V. Parcells, A. Margolis, R. K. Adair, and J. D. Clemens. 1991. The protective efficacy of polyvalent pneumococcal polysaccharide vaccine. N. Engl. J. Med. 325: 1453–1460.
10. Deich, R. A., B. J. Metcalf, C. W. Finn, J. E. Farley, and B. A. Green. 1988. Cloning of genes encoding a 15,000-dalton peptidoglycan-associated lipotrotein from *Haemophilus influenzae*. J. Biol. Chem. 263:9790–9794.
11. Sarnaik S., J. Kaplan, G. Schiffman, D. Bryla, J. B. Robbins, R. Scheerson. 1990. Studies on pneumococcus vaccine alone or mixed with DT and on pneumococcus type 6B and *Haemophilus influenzae* type b capsular polysaccharide-tetanus toxoid conjugates in 2- to 5-year old children with sikle cell anemia. Pediatr. Infect. Dis. J. 9:181–186.
12. Weinberg, G. A., D. A. Towler, and R. S. Munson, Jr. 1988. Lipoproteins of *Haemophilus influenzae* type b. J. Bacterol. 170:4161–4164.
13. Murphy, T. F., M. B. Nelson, K. C. Dudas, J. M. Mylotte, and M. A. Apicella. 1985. Identification of a specific epitope of *Haemophilus influenzae* on a 16,600-dalton outer membrane protein. J. Infec. Dis. 152:1300–1307.
14. Murphy, T. F., L. C. Bartos, A. M. Campagnari, M. B. Nelson, K. C. Dudas, and M. A. Apicella. 1986. Identification of a 16,600 dalton outer membrane protein of nontypeable *Haemophilus influenzae* as a target for human bactericidal antibody. J. Clin. Invest. 78:1020–1027.
15. Green, B. A., T. Quinn-Dey, and G. W. Zlothick. 1987. Biologic activities of antibody to a peptidoglycan-associated lipoprotein of *Haemophilus influenzae* against multiple clinical isolates of *H. influenzae* type b. Infect. Immun. 55:2878–2883.
16. Munson, R. S. Jr., and D. M. Granoff. 1985. Purification and partial characterization of outer membrane proteins P5 and P6 from *Haemophilus influenzae* type b. Infect. Immun. 49:544–549.
17. Bradford, M. M. 1976. A rapid method for the quantitation of microgram quantities of protein utilizing the principle of protein-dye binding. Anal. Biochem. 72:248–254.
18. Dubois, M., K. A. Gulles, J. K. Hamilton, P. A. Rebers, and F. Smith. 1956. Colorimetric method for the determination of sugars and related substances. Anal. Chem. 28:350–356.
19. Panezutti, H., 0. James, E. J. Hanson, Y. Choi, R. E. Harkness, M. H. Klein and P. Chong. 1993. Identification of surface-exposed B-cell epitopes recognized by *Haemophilus influenzae* type b P1-specific monoclonal antibodies. Infec. Immun. 61: 1867–1872.
20. WO 94/12641
21. WO 92/10936
22. US 5141743
23. Lockhoff, O. Glycolipids as Immunomodulators: Synthesis and Properties. 1991. Chem. Int. Ed. Engl. 30: 1611–11620.
24. Nixon-George, A., Moran, T., Dionne, G., Penney, C. L., Lafleur, D., Bona, C. A. The adjuvant effect of stearyl tyrosine on a recombinant subunit hepatitis B surface antigen. 1990 J. Immunol. 144: 4798–4802.
25. Wiesmüller, K.-H., Jung, G., Hess, G. Novel low-molecular weight synthetic vaccine against foot-and-mouth disease containing a potent B-cell and macrophage activator. 1989. Vaccine 8: 29–33.
26. Deres, et al. 1989, Nature 342: 651.
27. Jennings, H. J. Capsular Polysaccharides as Vaccine Candidates. 1990. Current Topics in Microbiology and Immunology 150: 97–127.
28. Porro et al 1983. J. Biol. Stand. 11: 65–71.
29. Brodeur, B. R., P. S. Tsang, J. Hamel, Y. Larose, S. Montplaisir. 1986. Mouse models of infection for *Neisseria meningitidis* B, 2b and *Haemophilus influenzae* type b diseases. Can. J. Microbiol. 32:33–37.

What we claim is:

1. A process for individually isolating P1, P2 and P6 outer membrane protein from a Haemophilus strain, comprising the steps of:

(a) providing a cell paste of the Haemophilus strain;
    (b) selectively extracting P2 protein from the cell paste to produce a first supernatant containing said P2 protein substantially free from P1 and P6 protein and a residual precipitate containing P1 and P6 protein;
    (c) separating the first supernatant from said residual precipitate;
    (d) concentrating the P2 protein in said first supernatant to produce a second supernatant;
    (e) purifying P2 protein in said second supernatant substantially free from pyrogens, lipopolysaccharides and other impurities solubilized from said paste by said selective extraction step;
    (f) selectively extracting P1 protein from the residual precipitate from step (b) to produce a third supernatant containing P1 protein and a P6-containing precipitate;
    (g) separating said third supernatant from said P6-containing precipitate;
    (h) concentrating the P1 protein in said third supernatant to produce a fourth supernatant;
    (i) purifying P1 protein in said fourth supernatant substantially free from pyrogens, lipopolysaccharides, P2 protein and other impurities solubilized in step (f);
    (j) selectively extracting the P6-containing precipitate to produce a P6-containing supernatant and a first extracted precipitate;
    (k) separating said P6-containing supernatant from said first extracted precipitate;
    (l) concentrating the P6 protein in said P6-containing supernatant to produce a fifth supernatant; and
    (m) purifying P6 protein in said fifth supernatant substantially free from pyrogens, lipopolysaccharides, P1 protein and other impurities solubilized in step (j).

2. The process of claim 1 wherein said selective extraction of P2 protein from cell paste is effected using an aqueous sodium chloride solution of about 0.2 to about 2 M.

3. The process of claim 1 wherein said P2 protein concentration step (d) comprises selective precipitation of P2 protein from said first supernatant to form a P2-containing precipitate and a sixth supernatant, separating this P2-containing precipitate from said sixth supernatant, selectively detergent extracting the P2-containing precipitate to solubilize the P2 protein and obtain a crude P2 extract as said second supernatant and a second extracted precipitate containing contaminants solubilized with said P2 protein in step (b), and separating said crude P2 extract from said second extracted precipitate.

4. The process of claim 3 wherein said Haemophilus strain is *Haemophilus influenzae* type b, polyribosylphosphate (PRP) is extracted from said cell paste in step (b) and said selective precipitation of P2 protein leaves the PRP in said sixth supernatant.

5. The process of claim 4 wherein said PRP is recovered and purified from said sixth supernatant.

6. The process of claim 3 wherein said purification step (e) includes selective removal of pyrogens from said P2-containing precipitate prior to said selective detergent extraction.

7. The process of claim 6 wherein said purification step (e) includes binding P2 protein in said crude P2 extract to a first chromatographic column, selectively eluting contaminants including pyrogens and LPS from said first chromatographic column while leaving P2 protein bound to the first chromatographic column, and subsequently eluting purified P2 protein from the first chromatographic column.

8. The process of claim 7 wherein said first chromatographic column comprises a hydroxyapatite matrix.

9. The process of claim 1 wherein said selective extraction of P1 protein from the residual precipitate in step (f) is effected by detergent extraction.

10. The process of claim 9 wherein said P1 protein concentration step (h) comprises selective precipitation of P1 protein from said third supernatant to form a P1-containing precipitate and a seventh supernatant, separating the P1-containing precipitate from said seventh supernatant, and detergent extracting the P1-containing precipitate to solubilize the P1 protein and obtain a crude P1 extract as said fourth supernatant.

11. The process of claim 10 wherein said purification step (i) includes binding P1 protein and P2 protein in said crude P1 extract to a second chromatographic column, selectively eluting said P1 protein from said second chromatographic column while leaving said P2 protein bound to said second chromatographic column to provide a first eluate, binding P1 protein in the first eluate from said second chromatographic column to a third chromatographic column, selectively eluting contaminants including pyrogens and LPS from said third chromatographic column while leaving P1 protein bound to the third chromatographic column, and subsequently eluting purified P1 protein from said third chromatographic column.

12. The process of claim 11 wherein P1 protein in the eluate from said second chromatographic column is concentrated prior to binding the P1 protein to said third chromatographic column.

13. The process of claim 12 wherein said second chromatographic column is a DEAE-Sephacel matrix and said third chromatographic column is a hydroxyapatite matrix.

14. The process of claim 1 wherein said selective extraction of P6 protein from the P6-containing precipitate in step (j) is effected by detergent extraction at an elevated temperature of about 40° C. to about 70° C.

15. The process of claim 14 wherein said P6 protein concentration step (1) comprises selective precipitation of P6 protein from said P6-containing supernatant to form a P6-containing precipitate and an eighth supernatant, separating the P6-containing precipitate from said eighth supernatant, and detergent extracting the P6-containing precipitate to solubilize the P6 protein and obtain a crude P6 extract as said fifth supernatant.

16. The process of claim 15 wherein said purification step (m) includes binding P6 protein and P1 protein in said crude P6 extract to a fourth chromatographic column, selectively eluting said P6 protein from said fourth chromatographic column while leaving said P1 protein bound to said fourth chromatographic column to provide a second eluate, binding P6 protein in the second eluate from said fourth chromatographic column to a fifth chromatographic column, selectively eluting contaminants including pyrogens and LPS from said fifth chromatographic column while leaving P6 protein bound to the fifth chromatographic column, and subsequently eluting purified P6 protein from said fifth chromatographic column.

17. The process of claim 16 wherein P6 protein in the eluate from said fourth chromatographic column is concentrated prior to binding the P6 protein to said fifth chromatographic column.

18. The process of claim 17 wherein said fourth chromatographic column is DEAE-Sephacel and said fifth chromatographic column is hydroxyapatite.

* * * * *